United States Patent
Wang

(10) Patent No.: US 10,500,071 B2
(45) Date of Patent: Dec. 10, 2019

(54) SENSOR DEVICE APPLIED IN ARTICULATION AND ARTIFICIAL LIMB SYSTEM WITH SENSOR DEVICE

(71) Applicant: BOE TECHNOLOGY GROUP CO., LTD., Beijing (CN)

(72) Inventor: Hong Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 100 days.

(21) Appl. No.: 15/521,583

(22) PCT Filed: Jun. 21, 2016

(86) PCT No.: PCT/CN2016/086552
§ 371 (c)(1),
(2) Date: Apr. 24, 2017

(87) PCT Pub. No.: WO2017/161712
PCT Pub. Date: Sep. 28, 2017

(65) Prior Publication Data
US 2018/0177616 A1    Jun. 28, 2018

(30) Foreign Application Priority Data
Mar. 25, 2016 (CN) .......................... 2016 1 0179850

(51) Int. Cl.
*A61F 2/48* (2006.01)
*A61F 2/30* (2006.01)
(Continued)

(52) U.S. Cl.
CPC .................. *A61F 2/68* (2013.01); *A61B 5/11* (2013.01); *A61B 5/1121* (2013.01);
(Continued)

(58) Field of Classification Search
CPC .. A61F 2002/30054; A61F 2002/30079; A61F 2210/009; A61F 2250/0045; G01R 33/072
(Continued)

(56) References Cited

U.S. PATENT DOCUMENTS

| 4,552,014 A | 11/1985 | Berchtold |
| 9,956,080 B1 * | 5/2018 | Howard .................... A61F 2/32 |
| 2015/0105782 A1 | 4/2015 | D'Lima et al. |

FOREIGN PATENT DOCUMENTS

| CN | 1074109 A | 7/1993 |
| CN | 101013039 A | 8/2007 |

(Continued)

OTHER PUBLICATIONS

Johnson, Mark W et al., "Implantable Transducer for Two-Degree of Freedom Joint Angle Sensing", Institute of Electrical and Electronics Engineers: Transactions on Rehabilitation Engineering, vol. 7, No. 3, Sep. 1999.
(Continued)

*Primary Examiner* — David H Willse
(74) *Attorney, Agent, or Firm* — Kinney & Lange, P.A.

(57) ABSTRACT

Embodiments of the present disclosure relate to the field of medical instrument, in particular to a sensor device applied in an articulation and an artificial limb system to improve control precision of the sensor. The sensor device of the present disclosure includes a plurality of magnets spaced apart from each other, the adjacent magnets having opposite polarities in a moving direction of the articulation; and at least one magnetic inductor for monitoring a displacement of the magnets caused by movement of the articulation.

13 Claims, 3 Drawing Sheets

(51) Int. Cl.
    *A61F 2/70*     (2006.01)
    *A61F 2/68*     (2006.01)
    *G01R 33/07*     (2006.01)
    *G01R 33/00*     (2006.01)
    *A61B 5/11*     (2006.01)
    *A61B 5/00*     (2006.01)
    *A61F 2/76*     (2006.01)

(52) U.S. Cl.
    CPC .......... *A61B 5/4571* (2013.01); *A61B 5/4851* (2013.01); *G01R 33/0005* (2013.01); *G01R 33/072* (2013.01); *A61B 5/1126* (2013.01); *A61B 5/6867* (2013.01); *A61B 2562/0223* (2013.01); *A61F 2002/482* (2013.01); *A61F 2002/6863* (2013.01); *A61F 2002/762* (2013.01); *A61F 2002/7625* (2013.01)

(58) Field of Classification Search
    USPC ....................................................... 623/18.12
    See application file for complete search history.

(56) References Cited

FOREIGN PATENT DOCUMENTS

| | | |
|---|---|---|
| CN | 101535772 A | 9/2009 |
| CN | 102490184 A | 6/2012 |
| CN | 102512270 A | 6/2012 |
| CN | 103494659 A | 1/2014 |
| CN | 105291139 A | 2/2016 |
| CN | 105509775 A | 4/2016 |

OTHER PUBLICATIONS

First Chinese Office Action, for Chinese Patent Application No. 201610179850.1, dated May 3, 2018, 10 pages.
International Search Report and Written Opinion (including English translation of Box V) dated Nov. 30, 2016, for corresponding PCT Application No. PCT/CN2016/086552.
Second Chinese Office Action, for Chinese Patent Application No. 201610179850.1, dated Nov. 13, 2018, 14 pages.

* cited by examiner

SENSOR DEVICE APPLIED IN ARTICULATION AND ARTIFICIAL LIMB SYSTEM WITH SENSOR DEVICE

CROSS-REFERENCE TO RELATED APPLICATION

This application claims the benefit of Chinese Patent Application No. 201610179850.1 filed on Mar. 25, 2016 in the State Intellectual Property Office of China, the whole disclosure of which is incorporated herein by reference.

FIELD OF THE INVENTION

Embodiments of the present disclosure relate to field of medical instrument, in particular to a sensor device applied in an articulation and an artificial limb with the sensor device.

DESCRIPTION OF THE RELATED ART

Currently, with the development of the medical technology, the requirements for medical instruments are getting higher and higher. An artificial limb is an important medical instrument and its practical value and control precision is one of key performance indicator. Although the current artificial limb is getting smarter and smarter, and its mass is getting lighter and lighter, control precision of a sensor device on the artificial limb is not high, which may not be convenient for the usage of an user installed with the artificial limb.

SUMMARY OF THE INVENTION

Embodiments of the present disclosure provide a sensor device applied in an articulation and an artificial limb system for at least alleviating the problem that the sensor of the artificial limb has poor control precision in the prior art.

According to one aspect of the present disclosure, there is provided a sensor device applied in an articulation comprising: a plurality of magnets spaced apart from each other, the adjacent magnets having opposite polarities in a moving direction of the articulation; and at least one magnetic inductor for monitoring displacement of the magnets caused by movement of the articulation.

According to an exemplary embodiment of the present disclosure, the sensor device further comprises a protective layer disposed between the plurality of magnets and the at least one magnetic inductor so as to protect the magnets and prevent a change in spacing between the magnets.

According to an exemplary embodiment of the present disclosure, the protective layer is made of the same material as that of a bone at the articulation.

According to an exemplary embodiment of the present disclosure, the plurality of magnets are disposed in a first bone at the articulation, and the at least one magnetic inductor is disposed on a surface of a second bone articulated with the first bone.

According to an exemplary embodiment of the present disclosure, each of the plurality of magnets is inserted into one of pores uniformly arranged on a surface of the first bone.

According to an exemplary embodiment of the present disclosure, the articulation has an articulate head located at the first bone and an acetabulum located at the second bone, or the articulation has an articulate head located at the second bone and an acetabulum located at the first bone.

According to an exemplary embodiment of the present disclosure, the magnets are in a form of a cylinder having a diameter of 0.08 mm±0.01 mm.

According to an exemplary embodiment of the present disclosure, the magnetic inductor comprises a Hall element.

According to an exemplary embodiment of the present disclosure, the plurality of magnets are arranged in a matrix structure substantially regularly arranged in a first direction in which the articulation moves and a second direction perpendicular to the first direction, and in the matrix structure, the adjacent magnets in each row in the first direction have opposite polarities to each other and all the magnets in each column in the second direction have the same polarity.

According to an exemplary embodiment of the present disclosure, the articulation is provided with two magnetic inductors arranged to be perpendicularly intersected with each other in the first and second directions respectively.

According to an exemplary embodiment of the present disclosure, the two magnetic inductors and the plurality of magnets have an initial position relationship in that projections of the two magnetic inductors on the surface of the first bone on which the plurality of magnets are placed are not overlapped with the plurality of the magnets.

According to an exemplary embodiment of the present disclosure, the sensor device further comprises a timer for recording a time during which the magnets are displaced.

According to another aspect of the present disclosure, there is provided an artificial limb system comprising the sensor device described above and at least two artificial limb bodies, in which the sensor device is located at an articulation formed by the artificial limb bodies.

BRIEF DESCRIPTION OF THE DRAWINGS

In order to clearly describe technical solution of embodiments of the present disclosure, the accompanying drawings necessary for describing the embodiments are illustrated below. Obviously, the accompanying drawings described below are merely some embodiments of the present disclosure, and those skilled in the art may obtain other accompanying drawings based on these drawings without any inventive steps.

DETAILED DESCRIPTION OF PREFERRED EMBODIMENTS OF THE INVENTION

In order to clarify the above object, technical schemes and advantages of the present disclosure, the present disclosure will be further described in detail below with reference accompanying drawings. Obviously, the described embodiments are merely some embodiments of the present disclosure, rather than all embodiments thereof. All other embodiments obtained by those ordinary skilled in the art without any inventive steps fall within the scope of the present disclosure.

The technical schemes of the present disclosure will be described in detail through particular embodiments thereof. However, the present disclosure is intended to include, but is not limited to, the following embodiments.

Figure 1:
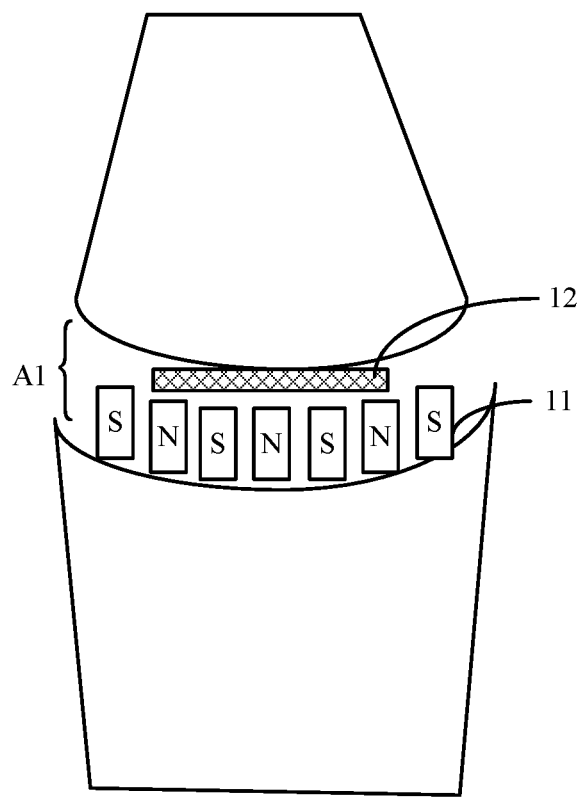
FIG. 1 is a schematic structural view of a sensor device applied in an articulation according to an exemplary embodiment of the present disclosure.

FIG. 1 is a schematic structural view of a sensor device applied in an articulation according to an exemplary embodiment of the present disclosure. As shown in FIG. 1, the sensor device comprises a plurality of magnets 11 provided at an articulation A1 and at least one magnetic inductor 12. The plurality of magnets 11 are spaced apart from each other, and the adjacent magnets 11 have opposite polarities. The magnetic inductor 12 is configured to monitor displacement of the magnets 11 caused by movement of the articulation.

By providing the plurality of magnets and the at least one magnetic inductor at the articulation, the displacement of the magnets can be monitored by the magnetic inductor when the articulation moves. Since the volumes of the magnets located at the articulation are relatively small, accuracy of the displacement measurement thereof is high such that the displacement of the articulation may be obtained more accurately.

Figure 2:
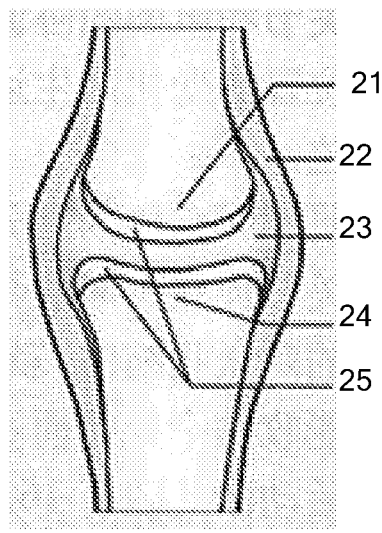
FIG. 2 is a schematic view of an example of an articulation of an organism.

FIG. 2 is a schematic view of an articulation of an organism as an example. The articulation comprises an articular head 21, an articular capsule 22, an articular cavity 23, an acetabulum 24 and an articular cartilage 25. The sensor device shown in FIG. 1 may be provided at the articulation. The articulation of the organism is connected with immovable bones and movable bones. Further, the articulation of the organism is not flat, but assumes a smooth concave or convex surface at articulated positions. Referring to FIG. 1, the plurality of magnets 11 are provided at the articulation, and these magnets 11 are spaced apart from each other, i.e., kept a predetermined distance therebetween. Further, the adjacent magnets 11 have opposite polarities to ensure that the magnetic inductor can detect magnetic fields of different directions and determine positions of the magnets based on the number of changes of the magnetic fields when the magnets move.

With this sensor device, displacements of the magnets caused by the movement of the articulation are detected in real time through an inductive effect of the magnetic inductor on the magnets. Since the positions of the magnets are relatively fixed at the beginning, it is possible to determine the number of the magnets passing through the magnetic inductor so as to determine the displacement of the magnets based on changes of magnetic fields induced by the magnetic inductor. Considering that volume of the magnets provided at the articulation is relatively small, thus the displacement obtained in this manner is relatively more accurate, which in turn provides convenience for subsequent displacement process. Further, the improved precision of the displacement facilitates improving accuracy of control process at the articulation.

In addition, considering that the sensor device is mainly applied in the articulation of the organism and the articular cavity at the articulation of the organism contains a synovial fluid, thus, the magnets may be covered with the synovial fluid or other connective tissues to protect the magnets.

According to an exemplary embodiment of the present disclosure, considering the utilization at the artificial limb articulation, in order to protect the magnets, avoid wear off and prevent change in spaces between the magnets, the sensor device further comprises a protective layer disposed between the plurality of magnets and the at least one magnetic inductor.

Figure 4:
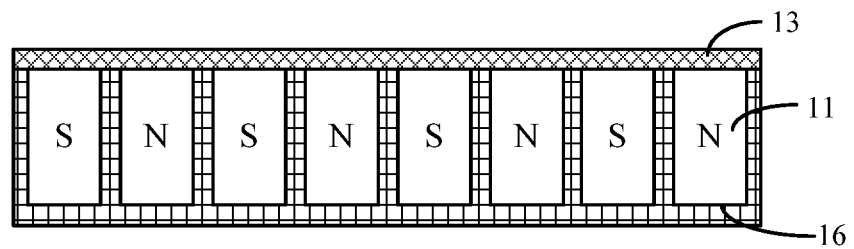
FIG. 4 is a sectional view of magnets provided in a first bone according to an exemplary embodiment of the present disclosure.

Particularly, referring to a sectional view of the magnets shown in FIG. 4, the protective layer 13 is generally disposed on a surface of the magnets 11 to cover and protect the magnets 11.

According to an exemplary embodiment of the present disclosure, in order to prevent surface rejection reaction, the protective layer 13 is made of the same material as that of the bones. In this way, the protective layer will be better compatible with an organism and not easily to generate the rejection reaction, thereby ensuring security.

In particular, in the actual implementation, the protective layer may be implanted at the articulation of the organism by a robot or other mini-operation arms. For example, a surface of the bone provided with the magnets is coated with a material same as that of the bone of the organism by means of coating. Alternatively, the surface of the bone provided with the magnets is bonded with a flexible thin film made of the same material as that of the bone of the organism by means of bonding. There are various implanting ways, and the present disclosure is not limited herein, and all available implanting ways fall within the scope of the present disclosure.

Figure 3:
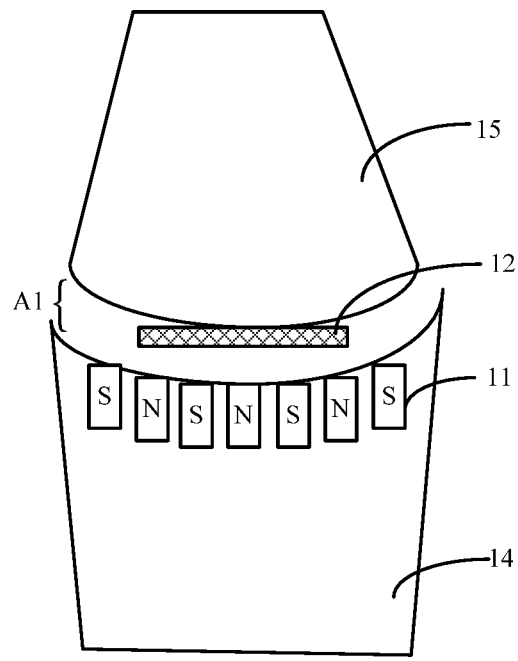
FIG. 3 is a schematic view of magnets and a magnetic inductor being respectively provided in different bones at an articulation according to an exemplary embodiment of the present disclosure.

According to an exemplary embodiment of the present disclosure, in order to better realize accurate monitoring, the magnets and the magnetic inductor may be disposed in different bones at the articulation, respectively. Particularly, as illustrated in FIG. 3, the plurality of magnets 11 are disposed in a first bone 14 at the articulation, and the at least one magnetic inductor 12 is disposed on a surface of a second bone 15 articulated with the first bone 14. As shown in FIG. 3, the first bone 14 has a concave structure, and the second bone 15 has a convex structure. The first bone 14 and the second bone 15 are spaced apart from each other by a predetermined distance and articulated with each other to form the articulation. The first bone 14 may be set as the artificial limb bone, and the second bone 15 may be set as the bone of the organism. Alternatively, both the first bone 14 and the second bone 15 may be set as the bones of the organism. Alternatively, both the first bone 14 and the second bone 15 may be set as the artificial limb bones. This can ensure the sensor device is provided steadily and will not offset due to the movement of the articulation, thereby further ensuring the accuracy.

Particularly, referring to the sectional view of the magnets shown in FIG. 4, each of the plurality of magnets 11 is inserted in one of pores 16 uniformly arranged on the surface of the first bone 14. Generally, each pore is in form of a cylinder and a depth thereof may be set according to the type of the bone. The depth is generally about twice of a diameter of the hole (about 0.1 mm). In addition, a space between the adjacent pores is preferably equal to each other to improve the accuracy when calculating the displacement by counting. This may prevent the spaces between the magnets from changing so that the uniform arrangement will facilitate an accurate displacement measurement.

When the pore is in the form of the cylindrical shape, each of the magnets also is in form of a cylinder having a diameter of 0.08 mm±0.01 mm. In this way, the magnets may have a small volume and the test accuracy is relative high.

Alternatively, if each magnet has a smaller dimension, the magnet may be a cube column, four corners of which are properly inserted into the pores. A surface of each magnet 11 is flushed with the surface of the first bone 14.

In various embodiments of the present disclosure, the magnets 11 and the magnetic inductor 12 may be provided at the articulation of the organism in the following first and second arrangements.

In the first arrangement, the articular head of the articulation is located at one end of the first bone, and the acetabulum is located at one end of the second bone opposite to the first bone. In this way, the magnets 11 may be inserted in the pores on a surface of the acetabulum, and the magnetic inductor 12 may be disposed on a surface of the acetabulum.

In the second arrangement, the articular head of the articulation is located at one end of the second bone, and the acetabulum is located at one end of the first bone opposite to the second bone. In this way, the magnets 11 may be inserted in the pores on a surface of the acetabulum, and the magnetic inductor 12 may be disposed on a surface of the articular head.

In fact, regardless the magnets are disposed on the articular head or on the acetabulum, the magnets 11 and the magnetic inductor 12 may achieve the function of detecting the displacement of magnets. For example, assuming the acetabulum is a movable articulation, and the articular head is an immovable articulation, when the magnets 11 and the magnetic inductor 12 are in the first arrangement, as the acetabulum at which the magnetic inductor 12 is placed moves, the magnets 11 will move relative to the magnetic inductor 12. At this time, the magnetic inductor 12 may also detect the displacement of the magnets during moving. Likewise, when the magnets 11 and the magnetic inductor 12 are in the second arrangement, as the acetabulum at which the magnets 11 are placed moves, the magnetic inductor 12 detects the displacement of the magnets during moving. Therefore, the magnets and the magnetic inductor are exchangeable in position, the displacement due to the movement of the articulation may be accurately measured as long as the relative displacement therebetween is determined.

In various embodiments of the present disclosure, the magnetic inductor 12 may be a Hall element. The Hall element is capable of counting according to a changing direction of magnetic inductive lines so as to determine the displacement.

Moreover, the magnetic inductor 12 may also be any one of a magneto-resistive diode, a magneto-sensitive transistor, a semiconductor-type magnetoresistive or a semiconductor-type sensor.

Figure 5:
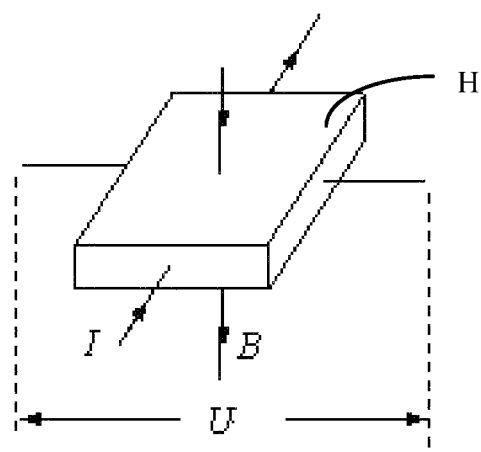
FIG. 5 is a schematic view of operation principle of a Hall element.

In particular, referring to FIG. 5 showing an operation principle of the Hall element, for a given Hall element H applied with a biasing current I, when the biasing current I is constant, a voltage U of the Hall element H is completely depended on intensity B of a magnetic field to be detected. With effect of Lorentz force, an electron flow of the biasing current I is offset toward one side of the Hall element H when flowing therethrough, so that the Hall element H generates a potential difference. The voltage U of the Hall element will vary as the intensity B of the magnetic field varies. The stronger the intensity of the magnetic field is, the higher the voltage is, and the weaker the intensity of the magnetic field is, the lower the voltage is. A polarity of the voltage varies as the direction of the magnetic field varies. For example, in a case where the Hall element H used as the magnetic inductor is disposed on the second bone 15 and the magnets are disposed on the first bone 14 as shown in FIG. 3, the magnets and the magnetic inductor will displace with respect to each other as the articulation moves. In this way, the magnetic field direction of the plurality of magnets undergoes a change with respect to the Hall element H and the Hall element H will detect the change in the direction of the magnetic field. The Hall element will take one count per change in the direction of the magnetic field. In this way, it is possible to detect the times of the change in the direction of the magnetic field. Further, since the spaces between the pores are substantially constant, the relative position between the magnets is fixed. Therefore, it is possible to obtain the displacement merely by calculating the number of the magnets moving through the Hall element H. Thus, it is possible to realize the monitoring of the displacement of the articulation.

Figure 6:
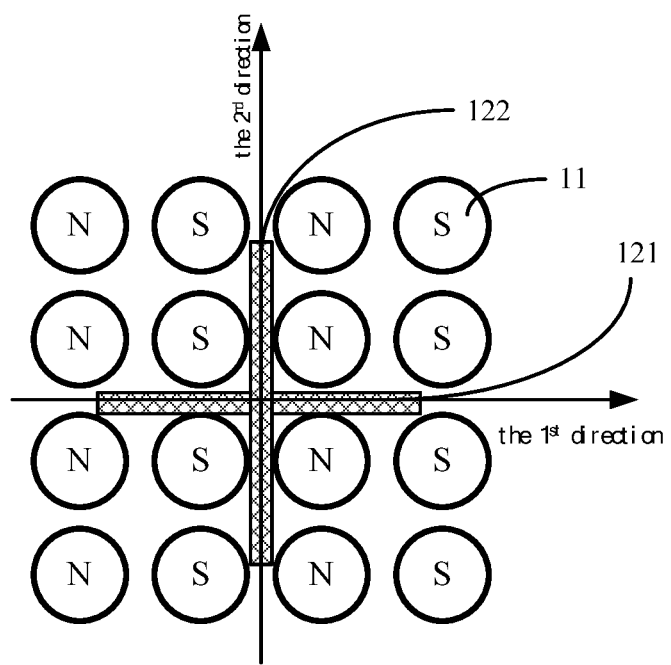
FIG. 6 is a top view of a sensor device applied in an articulation according to an exemplary embodiment of the present disclosure.

According to an exemplary embodiment of the present disclosure, as shown in FIG. 6, the articulation of the organism is provided with two magnetic inductors arranged to be perpendicularly intersected with each other. For example, one magnetic inductor 121 monitors the displacement of the magnets in a first direction, the displacement of this magnetic inductor is normally the displacement of the articulation to be tested finally. The other magnetic inductor 122 monitors the displacement of the magnets in a second direction perpendicular to the first direction. Thus, it is possible to detect the whole displacement of the magnets, thereby realizing an accurate measurement of the displacement of the articulation.

In addition, as shown in FIG. 6, the plurality of magnets 11 are arranged in a matrix structure substantially regularly arranged and in the matrix structure the adjacent magnets in each row in the first direction in which the articulation moves have opposite polarities to each other, and all the magnets in each column in the second direction have the same polarity. The arrangement of this embodiment contributes to increase the intensity of the magnetic field, thereby improving sensitivity of the sensor device.

In particular, based on the arrangement of the magnetic inductors shown in FIG. 6, an initial position relationship of the two magnetic inductors with the plurality of magnets 11 is configured so that projections of the two magnetic inductors on the surface of the first bone on which the plurality of magnets 11 are placed are not overlapped with the plurality of the magnets 11. In this way, it is possible to accurately detect the displacement. If the projections of the magnetic inductors are overlapped with the magnets, the measured displacement may not include the displacement of the overlapped magnets, which results in an inaccurate measurement. Therefore, it is preferable to ensure the projections of the magnetic inductors on the surface of the first bone are located at gaps between the magnets. In this way, the accuracy of the measurement may be guaranteed, and the inaccurate measurement due to the projection on the magnets will be avoided.

According to an exemplary embodiment of the present disclosure, after monitoring the displacement of articulation when moving, for example, through monitoring the displacement of the magnets caused by the movement of the articulation, this displacement will be processed by using an external timer to calculate parameters such as velocity, acceleration of the movement.

Considering a transferring delay of the external timer, in other embodiments, the sensor device may be provided with a built-in process chip such as built-in timer. The built-in timer is configured for recording a time during which the magnets are displaced, so as to quickly and accurately obtain the desired velocity, acceleration and the like to precisely control the articulation.

The sensor device as described in the above embodiments is applicable to the articulation of the organism or an artificial limb and thus has good flexibility in the application.

For example, the sensor device may be used to experimentally observe activity of the organism, to make a bionic research and to perform a minimally invasive therapy to a patient with motor nerve atrophy.

According to another aspect of the present disclosure, there is provided an artificial limb system comprising the sensor device as described in any one of the above embodiments and at least two artificial limb bodies. The sensor device is located at an articulation formed by the artificial limb bodies. It should be understood that the artificial limb system may comprise a plurality of articulations, each of which may be provided with the sensor device to flexibly and accurately control movement of the artificial limb bodies.

In the field of the artificial limb, the artificial limb system having the sensor device according to various embodiments of the present disclosure can accurately obtain the displacement at the articulation of the artificial limb so as to precisely control the movement of the artificial limb.

Although preferable embodiments of the present disclosure have been described, those skilled in the art can make other changes and modifications to those embodiments once reading the basic inventive concept. Thus, the appended claims are intended to be interpreted to include these preferable embodiments and all the changes and modifications falling within the scope of the present disclosure.

Obviously, those skilled in the art may make various changes and modifications without departing from the spirit and scope of the present disclosure. Thus, if these changes and modifications of the present disclosure fall within the scope claimed in claims and their equivalents, the present disclosure is intended to include these changes and modifications.

What is claimed is:

1. A sensor device configured to be applied in an articulation, the sensor device comprising:
   a plurality of magnets spaced apart from each other, adjacent magnets of the plurality of magnets having opposite polarities in a moving direction of the articulation; and
   at least one magnetic inductor for monitoring displacement of the magnets caused by movement of the articulation, wherein the at least one magnetic inductor is configured to detect magnetic fields of different directions and determine positions of the plurality of magnets based on a number of changes of the magnetic fields when the plurality of magnets move.

2. The sensor device according to claim 1, further comprising a protective layer disposed between the plurality of magnets and the at least one magnetic inductor so as to protect the magnets and prevent a change in spacing between the magnets.

3. The sensor device according to claim 2, wherein the protective layer is made of the same material as that of a bone at the articulation.

4. The sensor device according to claim 1, wherein the plurality of magnets are configured to be disposed in a first bone at the articulation, and the at least one magnetic inductor is configured to be disposed on a surface of a second bone articulated with the first bone.

5. The sensor device according to claim 4, wherein each of the plurality of magnets is configured to be inserted into one of a plurality of pores uniformly arranged on a surface of the first bone.

6. The sensor device according to claim 5, wherein
   the articulation has an articulate head located at the first bone and an acetabulum located at the second bone or
   the articulation has an articulate head located at the second bone and an acetabulum located at the first bone.

7. The sensor device according to claim 5, wherein the magnets are in a form of a cylinder having a diameter of 0.08 mm±0.01 mm.

8. The sensor device according to claim 1, wherein the at least one magnetic inductor comprises a Hall element.

9. The sensor device according to claim 8, wherein the plurality of magnets are arranged in a matrix structure substantially regularly arranged in a first direction in which the articulation moves and a second direction perpendicular to the first direction, and in the matrix structure the adjacent magnets in each row in the first direction have opposite polarities to each other and all the magnets in each column in a second direction have the same polarity.

10. The sensor device according to claim 9, wherein the sensor device is configured so that the articulation can be provided with two magnetic inductors arranged to be perpendicularly intersected with each other in the first and second directions respectively.

11. The sensor device according to claim 10, wherein the two magnetic inductors and the plurality of magnets have an initial position relationship in that projections of the two magnetic inductors on the surface of a first bone on which a plurality of magnets are placed are not overlapped with the plurality of the magnets.

12. The sensor device according to claim 11, further comprising a timer for recording a time during which the magnets are displaced.

13. An artificial limb system comprising the sensor device according to claim 1 and at least two artificial limb bodies, wherein the sensor device is located at an articulation formed by the artificial limb bodies.

* * * * *